United States Patent
Andronic

(10) Patent No.: US 9,540,770 B2
(45) Date of Patent: Jan. 10, 2017

(54) MODULAR SENSING SYSTEM FOR WEB-BASED APPLICATIONS

(71) Applicant: Honeywell ASCa Inc., Mississauga (CA)

(72) Inventor: Cristian Andronic, Burnaby (CA)

(73) Assignee: Honeywell Limited, Mississauga (CA)

( * ) Notice: Subject to any disclaimer, the term of this patent is extended or adjusted under 35 U.S.C. 154(b) by 0 days.

(21) Appl. No.: 14/497,057

(22) Filed: Sep. 25, 2014

(65) Prior Publication Data
US 2016/0090691 A1 Mar. 31, 2016

(51) Int. Cl.
*D21F 7/06* (2006.01)
*D21G 9/00* (2006.01)
(Continued)

(52) U.S. Cl.
CPC . *D21F 7/00* (2013.01); *D21F 7/06* (2013.01); *D21G 9/00* (2013.01); *G01D 11/00* (2013.01);
(Continued)

(58) Field of Classification Search
CPC ............. H04N 2201/04794; H04N 2201/0471; H04N 2201/04753; H04N 2201/04755; H04N 2201/04734; H04N 1/053; H04N 1/128; H04N 1/203; D21G 9/0027; D21G 9/0009; D21G 1/0093; D21G 9/0036; D21G 9/00; G01N 21/86; G01N 33/346; G01N 21/3559; G01N 21/8901; G01N 21/8903; G01N 2201/101; G01N 33/36; G01N 33/34; G01N 33/343; G01N 21/89; G01N 2021/8909; D21F 7/003; D21F 7/06; D21F 1/0027; D21F 1/02; D21F 1/06; D21F 7/008; Y10S 162/11; Y10S 162/06; Y10S 162/10; G01D 11/30
(Continued)

(56) References Cited

U.S. PATENT DOCUMENTS 3,465,550 A * 9/1969 Strom ................. G01N 21/314
162/17
3,673,865 A * 7/1972 Michaelsen ............ G01B 21/08
162/198
(Continued)

FOREIGN PATENT DOCUMENTS

DE       3533275 A1    3/1987

OTHER PUBLICATIONS

Notification of Transmittal of the International Search Report and the Written Opinion of the International Searching Authority, or the Declaration dated Dec. 2, 2015 in connection with International Patent Application No. PCT/CA2015/000499.

Primary Examiner — Eric Hug

(57) ABSTRACT

A system includes at least one common support configured to span at least a width of a web of material in a manufacturing or processing system. The system also includes multiple sensor heads each configured to move independently along at least part of the at least one common support. The sensor heads can be configured to move simultaneously along the at least one common support, and at least one controller can be configured to control movement of the sensor heads so that the sensor heads do not contact one another. Each sensor head could include one or more sensors configured to measure one or more characteristics of the web. Different sensor heads could include different types of sensors. The sensor heads can be configured to move in non-overlapping patterns over or under the web. Different sensor heads can be configured to move at different speeds.

21 Claims, 6 Drawing Sheets

(51) Int. Cl.
*G01D 11/30* (2006.01)
*G01N 33/34* (2006.01)
*G01N 21/89* (2006.01)
*D21F 7/00* (2006.01)
*G01D 11/00* (2006.01)

(52) U.S. Cl.
CPC .............. *G01N 21/89* (2013.01); *G01N 33/34* (2013.01); *G01N 2021/8909* (2013.01)

(58) Field of Classification Search
USPC .. 162/198, 263, 262, 252, 253, 259, DIG. 6, 162/DIG. 10, DIG. 11; 73/159, 73; 250/339.1, 559.01, 339.02, 559.04, 250/559.06; 700/127–129; 356/429–431
See application file for complete search history.

(56) References Cited

U.S. PATENT DOCUMENTS

| | | | | |
|---|---|---|---|---|
| 3,724,732 A | * | 4/1973 | Bonner | 226/21 |
| 3,936,665 A | * | 2/1976 | Donoghue | 700/129 |
| 4,271,699 A | * | 6/1981 | Williamson | G01B 7/107 33/501.02 |
| 4,500,968 A | * | 2/1985 | Bialkowski | 700/128 |
| 4,841,156 A | * | 6/1989 | May et al. | 250/461.1 |
| 4,910,688 A | * | 3/1990 | Amini | G01R 23/16 700/129 |
| 5,022,966 A | * | 6/1991 | Hu | D21G 9/0009 162/198 |
| 5,166,748 A | * | 11/1992 | Dahlquist | 356/451 |
| 5,262,955 A | * | 11/1993 | Lewis | 700/129 |
| 5,286,348 A | * | 2/1994 | Perin | 162/262 |
| 5,327,770 A | * | 7/1994 | Hindle | G01N 21/86 73/1.88 |
| 5,622,602 A | * | 4/1997 | Yakabe et al. | 162/252 |
| 5,654,799 A | * | 8/1997 | Chase et al. | 356/600 |
| 5,685,955 A | * | 11/1997 | Leigraf et al. | 162/198 |
| 5,714,763 A | * | 2/1998 | Chase et al. | 250/559.3 |
| 5,773,714 A | * | 6/1998 | Shead | 73/105 |
| 5,943,906 A | * | 8/1999 | Shakespeare | G01N 33/346 73/159 |
| 5,991,046 A | * | 11/1999 | Shakespeare et al. | 356/429 |
| 6,080,278 A | * | 6/2000 | Heaven et al. | 162/198 |
| 6,162,331 A | * | 12/2000 | Ruf et al. | 162/198 |
| 6,281,679 B1 | * | 8/2001 | King et al. | 324/229 |
| 6,398,914 B1 | * | 6/2002 | Furumoto | 162/198 |
| 6,538,743 B2 | * | 3/2003 | Shakespeare | G01N 21/89 356/429 |
| 6,640,152 B1 | * | 10/2003 | Chen et al. | 700/128 |
| 6,743,337 B1 | * | 6/2004 | Ischdonat | 162/198 |
| 6,805,772 B2 | * | 10/2004 | Schwarz | 162/198 |
| 6,809,756 B1 | * | 10/2004 | Valkonen et al. | 348/88 |
| 7,146,238 B2 | * | 12/2006 | Burma | 700/127 |
| 7,190,495 B2 | * | 3/2007 | Lam | H04N 1/1013 358/474 |
| 7,431,800 B2 | * | 10/2008 | Ferm et al. | 162/259 |
| 7,494,567 B2 | * | 2/2009 | Haran | D21F 7/003 162/198 |
| 7,496,413 B2 | * | 2/2009 | Fan et al. | 700/29 |
| 7,513,975 B2 | * | 4/2009 | Burma | 162/263 |
| 7,599,427 B2 | * | 10/2009 | Bik | 375/219 |
| 7,811,417 B2 | * | 10/2010 | MacHattie et al. | 162/263 |
| 7,959,763 B2 | * | 6/2011 | MacHattie et al. | 162/198 |
| 8,017,927 B2 | * | 9/2011 | Shakespeare | B41F 33/0045 250/559.04 |
| 8,196,516 B2 | * | 6/2012 | Beselt | 104/95 |
| 8,219,025 B2 | * | 7/2012 | Andronic | 455/41.1 |
| 8,248,610 B2 | * | 8/2012 | Kokko | D21G 9/0036 356/429 |
| 8,561,468 B2 | * | 10/2013 | Beselt et al. | 73/570 |
| 8,564,851 B2 | * | 10/2013 | Beselt | 358/474 |
| 8,728,276 B2 | * | 5/2014 | Shakespeare | 162/198 |
| 9,354,090 B2 | * | 5/2016 | Beselt | G01D 11/30 |
| 2003/0222219 A1 | * | 12/2003 | Almi | D21F 7/003 250/341.2 |
| 2006/0185809 A1 | * | 8/2006 | Elfrink et al. | 162/198 |
| 2007/0151689 A1 | * | 7/2007 | Beselt | 162/198 |
| 2007/0255446 A1 | * | 11/2007 | Backstrom et al. | 700/128 |
| 2008/0073050 A1 | * | 3/2008 | Muench | 162/198 |
| 2008/0308244 A1 | * | 12/2008 | Natori | 162/198 |
| 2009/0099682 A1 | * | 4/2009 | Jasinski | 700/128 |
| 2009/0237749 A1 | * | 9/2009 | Clouse | G05B 19/19 358/474 |
| 2012/0293669 A1 | * | 11/2012 | Mann | G01C 11/025 348/207.11 |
| 2013/0100503 A1 | * | 4/2013 | Beselt | 358/474 |
| 2013/0268226 A1 | * | 10/2013 | Morfino et al. | 702/94 |
| 2014/0345376 A1 | * | 11/2014 | Andronic et al. | 73/159 |
| 2014/0345397 A1 | * | 11/2014 | Beselt et al. | 73/866.5 |
| 2014/0348154 A1 | * | 11/2014 | Hofman et al. | 370/350 |

* cited by examiner

MODULAR SENSING SYSTEM FOR WEB-BASED APPLICATIONS

TECHNICAL FIELD

This disclosure relates generally to web manufacturing and processing systems. More specifically, this disclosure relates to a modular sensing system for paper and other web-based applications.

BACKGROUND

Sheets or other webs of material are used in a variety of industries and in a variety of ways. These materials can include paper, multi-layer paperboard, and other products manufactured or processed in long webs. As a particular example, long sheets of paper can be manufactured and collected in reels.

It is often necessary or desirable to measure one or more properties of a web of material as the web is being manufactured or processed. Adjustments can then be made to the manufacturing or processing system to ensure that the properties stay within desired ranges. Measurements are often taken using scanning sensors that move back and forth across the width of the web.

SUMMARY

This disclosure describes a modular sensing system for paper and other web-based applications.

In a first embodiment, a system includes at least one common support configured to span at least a width of a web of material in a manufacturing or processing system. The system also includes multiple sensor heads each configured to move independently along at least part of the at least one common support.

In a second embodiment, an apparatus includes a first sensor head configured to move along at least one common support spanning at least a width of a web of material in a manufacturing or processing system. The first sensor head includes one or more sensors configured to measure one or more characteristics of the web. The first sensor head also includes a controller configured to cause the first sensor head to move along at least part of the at least one common support independently of a second sensor head on the at least one common support.

In a third embodiment, a method includes independently moving first and second sensor heads back and forth along at least one common support. The method also includes measuring one or more characteristics of a web of material using the first and second sensor heads.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 7, discussed below, and the various embodiments used to describe the principles of this disclosure are by way of illustration only and should not be construed in any way to limit the scope of the concepts disclosed herein. Those skilled in the art will understand that the principles of this disclosure may be implemented in any type of suitably arranged device or system.

Figure 1:
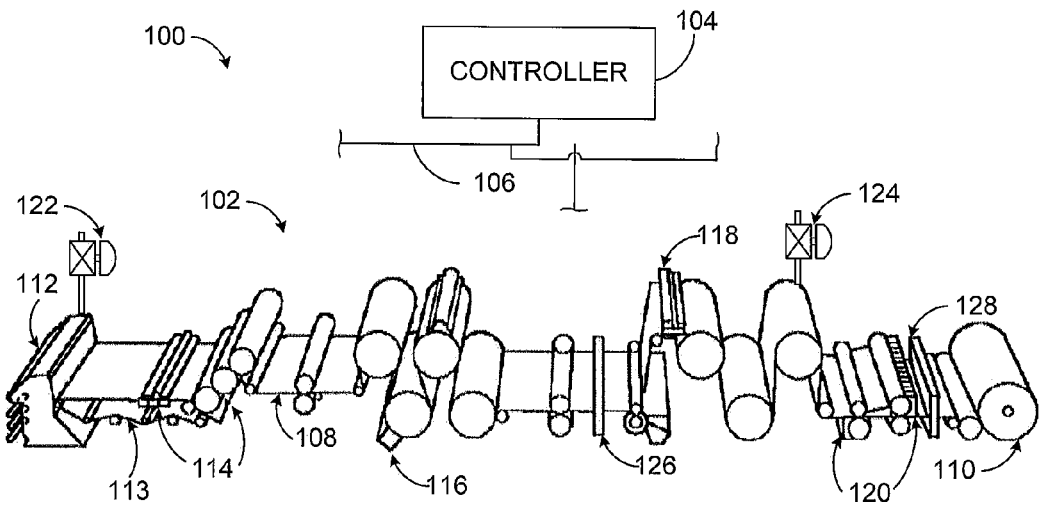
FIG. 1 illustrates an example web manufacturing or processing system according to this disclosure.

FIG. 1 illustrates an example web manufacturing or processing system 100 according to this disclosure. In this example, the system 100 includes a paper machine 102, a controller 104, and a network 106. The paper machine 102 includes various components used to produce a paper product, namely a paper web 108 that is collected at a reel 110. The controller 104 monitors and controls the operation of the paper machine 102, which may help to maintain or increase the quality of the paper web 108 produced by the paper machine 102.

In this example, the paper machine 102 includes at least one headbox 112, which distributes a pulp suspension uniformly across the machine onto a continuous moving wire screen or mesh 113. The pulp suspension entering the headbox 112 may contain, for example, 0.2-3% wood fibers, fillers, and/or other materials, with the remainder of the suspension being water. The headbox 112 may include an array of dilution actuators, which distributes dilution water into the pulp suspension across the web. The dilution water may be used to help ensure that the resulting paper web 108 has a more uniform basis weight across the web 108.

Arrays of drainage elements 114, such as vacuum boxes, remove as much water as possible to initiate the formation of the web 108. An array of steam actuators 116 produces hot steam that penetrates the paper web 108 and releases the latent heat of the steam into the paper web 108, thereby increasing the temperature of the paper web 108 in sections across the web. The increase in temperature may allow for easier removal of remaining water from the paper web 108. An array of rewet shower actuators 118 adds small droplets of water (which may be air atomized) onto the surface of the paper web 108. The array of rewet shower actuators 118 may be used to control the moisture profile of the paper web 108, reduce or prevent over-drying of the paper web 108, or correct any dry streaks in the paper web 108.

The paper web 108 is then often passed through a calender having several nips of counter-rotating rolls. Arrays of induction heating actuators 120 heat the shell surfaces of various ones of these rolls. As each roll surface locally heats up, the roll diameter is locally expanded and hence increases nip pressure, which in turn locally compresses the paper web 108. The arrays of induction heating actuators 120 may therefore be used to control the caliper (thickness) profile of the paper web 108. The nips of a calender may also be equipped with other actuator arrays, such as arrays of air showers or steam showers, which may be used to control the gloss profile or smoothness profile of the paper web.

Two additional actuators 122-124 are shown in FIG. 1. A thick stock flow actuator 122 controls the consistency of incoming stock received at the headbox 112. A steam flow actuator 124 controls the amount of heat transferred to the paper web 108 from drying cylinders. The actuators 122-124 could, for example, represent valves controlling the flow of stock and steam, respectively. These actuators 122-124 may be used for controlling the dry weight and moisture of the paper web 108.

Additional components could be used to further process the paper web 108, such as a supercalender (for improving the paper web's thickness, smoothness, and gloss) or one or more coating stations (each applying a layer of coatant to a surface of the paper to improve the smoothness and printability of the paper web). Similarly, additional flow actuators may be used to control the proportions of different types of pulp and filler material in the thick stock and to control the amounts of various additives (such as retention aid or dyes) that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, this disclosure is not limited to use with systems for producing paper products and could be used with systems that process a paper product or with systems that produce or process other items or materials (such as multi-layer paperboard, cardboard, plastic, textiles, plastic foils, films, laminates, metal webs, or other or additional materials that are manufactured or processed as moving webs).

In order to control the paper-making process, one or more properties of the paper web 108 may be continuously or repeatedly measured. The web properties can be measured at one or more various stages in the manufacturing process. This information may then be used to adjust the paper machine 102, such as by adjusting various actuators within the paper machine 102. This may help to compensate for any variations of the web properties from desired targets, which may help to ensure the quality of the web 108.

As shown in FIG. 1, the paper machine 102 includes one or more scanners 126-128, each of which may include one or more sensors. Each scanner 126-128 is capable of measuring one or more characteristics of the paper web 108. For example, each scanner 126-128 could include sensors for measuring the caliper, anisotropy, basis weight, color, gloss, sheen, haze, surface features (such as roughness, topography, or orientation distributions of surface features), or any other or additional characteristics of the paper web 108. Each scanner 126-128 includes any suitable structure or structures for measuring one or more characteristics of the paper web 108. For instance, each scanner 126-128 could include one or more sensor assemblies mounted on a rail, frame, or other support, where each sensor assembly includes one or more sets of sensors that move back and forth across all or a portion of the web 108.

The controller 104 receives measurement data from the scanners 126-128 and uses the data to control the paper machine 102. For example, the controller 104 may use the measurement data to adjust any of the actuators or other components of the paper machine 102. The controller 104 includes any suitable structure for controlling the operation of at least part of the paper machine 102, such as a computing device.

The network 106 is coupled to the controller 104 and various components of the paper machine 102 (such as the actuators and scanners). The network 106 facilitates communication between components of the system 100. The network 106 represents any suitable network or combination of networks facilitating communication between components in the system 100. The network 106 could, for example, represent a wired or wireless Ethernet network, an electrical signal network (such as a HART or FOUNDATION FIELDBUS network), a pneumatic control signal network, or any other or additional network(s).

In general, at least one of the scanners 126-128 includes at least one primary sensor head that moves back and forth across a surface of the web 108. The primary sensor head typically moves across the width of the web 108 on a rail, frame, or other support in the "cross direction" (CD). There may be a single primary sensor head that moves across the entire width of the web 108 or multiple primary sensor heads that each moves across a part of the width of the web 108. There could also be one or more primary sensor heads located on different sides (such as above and below) of the web 108.

A primary sensor head often travels back and forth hundreds of thousands or even millions of times during its operational lifespan. A primary sensor head may also include multiple sensors, such as sensors configured to measure different characteristics of a web, and the primary sensor head may travel back and forth many times without utilizing one or more of its sensors. However, even if particular sensors are not utilized, the unutilized sensors are still powered up and exposed to environmental conditions, which can degrade the sensor components' lifetimes and performances. Moreover, one or more sensors of a primary sensor head may need repair or maintenance. Even if other sensors of the primary sensor head do not need repair or maintenance, the entire primary sensor head assembly may need to be repaired or replaced. As a result, measurements cannot be taken using the functioning sensors of the primary sensor head during the repair or maintenance. In addition, in some systems, such as during product specification changes (often called "grade changes"), additional characteristics not capable of being measured by a sensor on a primary sensor head may be targeted for monitoring. To monitor for these characteristics, a primary sensor head may need to be replaced with a sensor head that includes the proper sensors, or the proper sensors may need to be added (if possible) to an existing primary sensor head.

As described in more detail below, these or other problems can be reduced or eliminated using at least one primary sensor head and at least one stand-alone sensor head on a common rail, frame, or other support. In some embodiments, a primary sensor head can include only the most commonly used sensors, while less commonly used sensors can be implemented in one or more stand-alone sensor heads. Thus, if the less commonly used sensors are not needed for a particular process, the primary sensor head can be powered up and exposed to environmental conditions while the stand-alone sensor heads are not, helping to reduce their exposure to conditions that can degrade the stand-alone sensor head components' lifetimes and performances. Moreover, if a stand-alone sensor head needs repair or maintenance, another stand-alone sensor head with the same type(s) of sensor(s) can be used during the repair or maintenance to help reduce or minimize process interruptions.

Additionally, if a primary sensor head has a sensor that needs repair or maintenance, a stand-alone sensor head with the same type(s) of sensor(s) can be added for use during the repair or maintenance. Finally, upon product specification changes, additional characteristics not capable of being measured by the primary sensor head may be targeted for monitoring and measuring using at least one stand-alone sensor.

Additional details regarding example uses of primary and stand-alone sensor heads are provided below. Note that the terms "primary" and "stand-alone" here are meant to distinguish between different types of sensor heads only and do not impart any type of structural limitations to those sensor heads. For instance, there is no requirement that a "primary" sensor head be larger than or carry more sensors than a "stand-alone" sensor head.

Although FIG. 1 illustrates one example of a web manufacturing or processing system 100, various changes may be made to FIG. 1. For example, other systems could be used to produce other paper or non-paper products. Also, while shown as including a single paper machine 102 with various components and a single controller 104, the system 100 could include any number of paper machines or other machinery having any suitable structure, and the system 100 could include any number of controllers. In addition, FIG. 1 illustrates one operational environment in which multiple sensor heads operate on a common rail, frame, or other support. This functionality could be used in any other type of system, and that system need not manufacture or process moving webs or webs.

Figure 2:
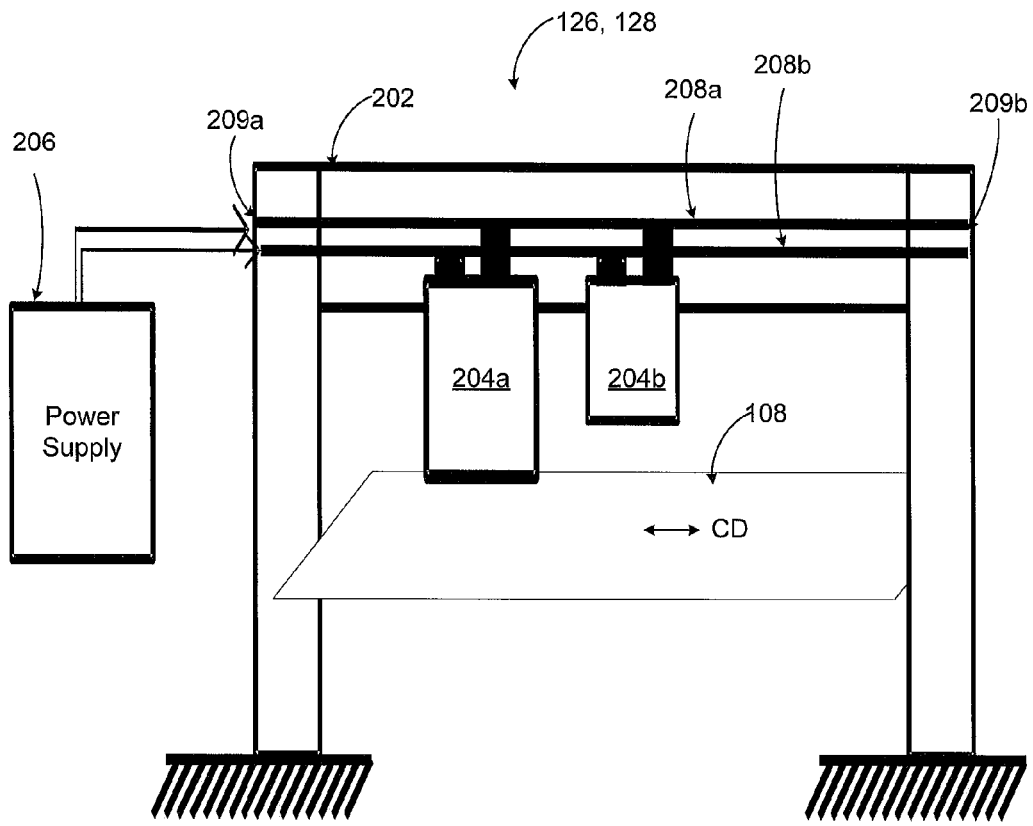
FIG. 2 illustrates a first example arrangement of sensors on a common support of a scanner according to this disclosure.

FIG. 2 illustrates a first example arrangement of sensors on a common support of a scanner according to this disclosure. For ease of explanation, this arrangement of sensors is described with respect to the scanner 126 or the scanner 128 in the system 100 of FIG. 1. However, this arrangement of sensors could be used with any suitable scanner and in any suitable system.

As shown in FIG. 2, the scanner 126, 128 includes a frame 202, which represents a structure that defines a space in which a web 108 can pass. The space within the frame 202 also includes various other components of the scanner. The frame 202 can be formed from any suitable material(s), such as metal. The frame 202 can also be formed in any suitable manner, such as welding. In addition, while shown here as being secured to the ground, the frame 202 could be secured to any other suitable structure.

The scanner 126, 128 also includes at least one primary sensor head 204*a* and at least one stand-alone sensor head 204*b*. Each primary sensor head 204*a* generally includes one or more sensors each capable of measuring at least one characteristic of the web 108. For example, each primary sensor head 204*a* could include sensors for measuring the moisture, caliper, anisotropy, basis weight, color, gloss, sheen, haze, surface features (such as roughness, topography, or orientation distributions of surface features), or any other or additional characteristics of the web 108. Each primary sensor head 204*a* includes any suitable structure or structures for measuring one or more characteristics of a web.

Similarly, each stand-alone sensor head 204*b* could include one or more sensors each capable of measuring at least one characteristic of the web 108. For example, each stand-alone sensor head 204*b* could include sensors for measuring the moisture, caliper, anisotropy, basis weight, color, gloss, sheen, haze, surface features (such as roughness, topography, or orientation distributions of surface features), or any other or additional characteristics of the web 108. Each sensor head 204*b* includes any suitable structure or structures for measuring one or more characteristics of a web. In some embodiments, each stand-alone sensor head 204*b* can include one or multiple sensors, and a primary sensor head 204*a* can include more sensors than the stand-alone sensor head(s) 204*b*.

In this example, at least one power supply 206 provides operating power to the sensor heads 204*a*-204*b*. Each power supply 206 represents any suitable source of operating power for one or more sensor heads. In this example, the power supply 206 provides operating power to the sensor heads 204*a*-204*b* via rails 208*a*-208*b*, although this need not be the case. For instance, each of the sensor heads 204*a*-204*b* could also or alternatively include internal power supplies.

The sensor heads 204*a*-204*b* generally move in the cross direction via a common support structure, which in this example represents a common set of rails 208*a*-208*b*. The rails 208*a*-208*b* can represent the primary or only support for the sensor heads 204*a*-204*b*. In other words, the sensor heads 204*a*-204*b* can ride on the rails 208*a*-208*b* and need no other external support.

As previously discussed, the primary sensor head 204*a* and the stand-alone sensor head 204*b* move in the cross direction along the width of the web 108. In some embodiments, one of the sensor heads 204*a*-204*b* moves only when the other sensor heads do not. In other embodiments, multiple sensor heads 204*a*-204*b* could move at the same time over different portions of a web 108. In general, multiple sensor heads 204*a*-204*b* could be configured to operate simultaneously or serially in any suitable manner. As a particular example, the stand-alone sensor head 204*b* can be set in an off or idle state when the stand-alone sensor head 204*b* is not needed to measure a particular parameter of the web 108. In this state, the stand-alone sensor head 204*b* can be disposed along the rails 208*a*-208*b* in a position where the stand-alone sensor head 204*b* cannot read a parameter of the web 108. For instance, the stand-alone sensor head 204*b* can be positioned at either end 209*a* or 209*b* of the rails 208*a*-208*b*, which allows the primary sensor head 204*a* to move along the entire width of the web 108. Similarly, the primary sensor head 204*a* can be set in an off or idle state when the primary sensor head 204*a* is not needed to measure a particular parameter of the web 108. The primary sensor head 204*a* can be positioned at either end 209*a* or 209*b*, which allows the stand-alone sensor head 204*b* to move along the entire width of the web 108.

Note that a sensor head 204*a* or 204*b* may or may not move completely off a web 108 when the sensor head is in an idle or off state. In other words, a sensor head may or may not occupy space above or below the web 108 when the sensor head is in an idle or off state. Thus, for example, a remaining sensor that is not in the idle or off state can move along a substantial cross-section of the web 108 but not including the portion occupied by the sensor in the idle or off state.

The primary sensor head 204*a* and the stand-alone sensor head 204*b* can be communicatively coupled or linked to one another or to one or more external components. For example, the sensor heads 204*a*-204*b* can be communicatively linked to a controller (such as the controller 104) and each other. As a particular example, each sensor head 204*a*-204*b* could identify or determine its current position, its anticipated position, its current speed, its current direction of movement, or an anticipated speed or direction of movement of other sensor(s). This could provide the sensor heads 204*a*-204*b* with an ability to simultaneously and independently move across the width (or a portion of the width) of the web 108 without making contact with or damaging the other sensor(s). In an embodiment, the sensor heads 204a-204b can be in contact with each other and move along at least one of the rails 208a or 208b together without interfering with each other.

Although FIG. 2 illustrates a first example of an arrangement of sensors on a common support of a scanner 126, 128, various changes may be made to FIG. 2. For example, while the sensor heads 204a-204b are shown as effectively "hanging off" the rails 208a-208b, the rails 208a-208b could be located under the sensor heads 204a-204b, or the sensor heads 204a-204b could have some other arrangement with the rails 208a-208b. Also, the scanner could include any number of primary and stand-alone sensor heads.

Figure 3A:
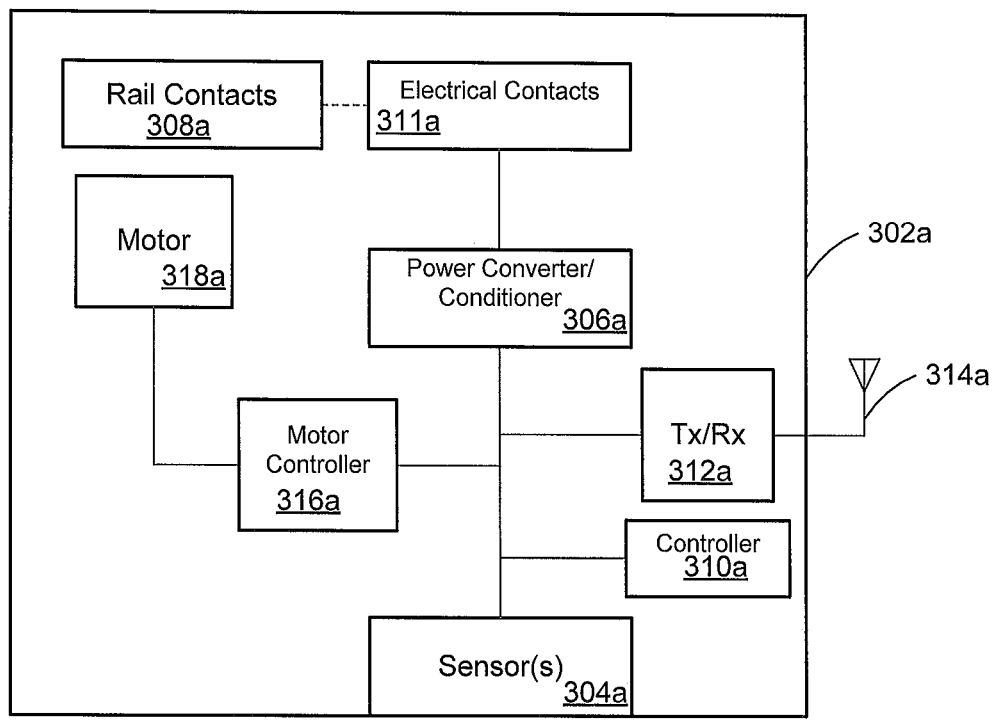
FIGS. 3A and 3B illustrate example sensor heads of a scanner according to this disclosure.
Figure 3B:
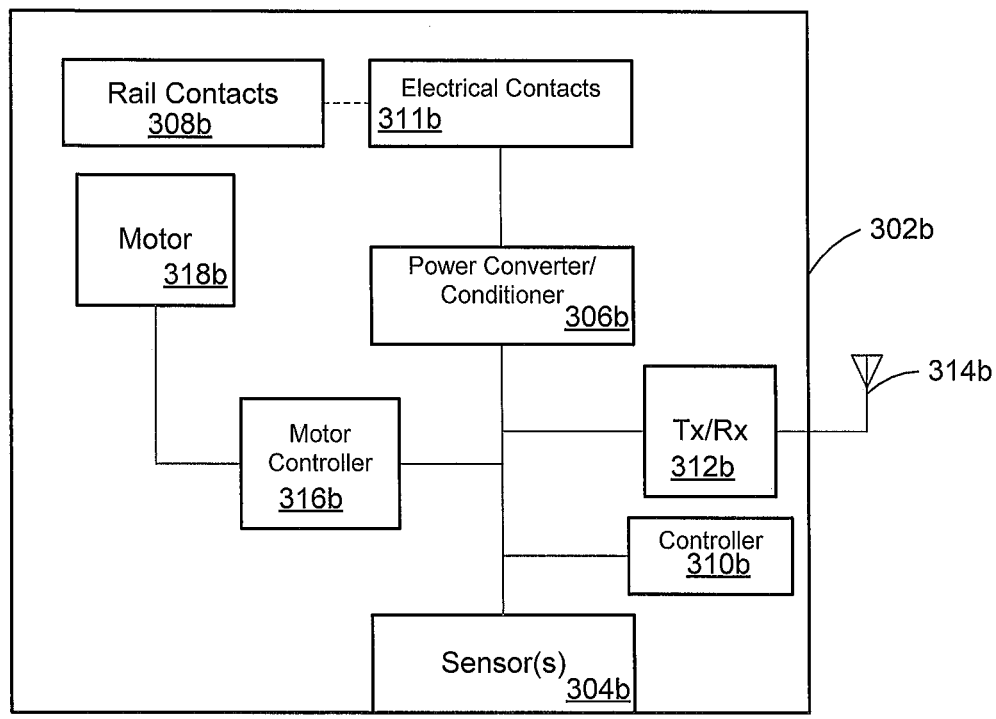

FIGS. 3A and 3B illustrate example sensor heads of a scanner according to this disclosure. In particular, FIG. 3A illustrates an example primary sensor head 204a, and FIG. 3B illustrates an example stand-alone sensor head 204b. For ease of explanation, the sensor heads 204a-204b are described with respect to the scanner 126 or the scanner 128 in the system 100 of FIG. 1. However, the sensor heads 204a-204b could be used with any suitable scanner and in any suitable system.

As shown in FIGS. 3A and 3B, each sensor head 204a-204b includes a moveable chassis 302a-302b, which represents a housing or other structure configured to encase, contain, or otherwise support other components of the sensor head 204a-204b. Each chassis 302a-302b can be formed from any suitable material(s) (such as metal) and in any suitable manner.

Each sensor head 204a-204b also includes one or more sensors 304a-304b that capture measurements associated with the web 108 or other material(s). For example, a primary sensor head 204a can include multiple sensors that are frequently used for a particular web material, while a stand-alone sensor head 204b can include fewer sensors that are used less frequently than the sensors in the primary sensor head 204a. In some embodiments, a stand-alone sensor head 204b can have a single sensor 304b dedicated to measuring a particular characteristic of a web 108. Each sensor 304a-304b includes any suitable structure for capturing measurements associated with one or more characteristics of a web. A sensor 304a-304b could represent a contact sensor that takes measurements of a web via contact with the web or a non-contact sensor that takes measurements of a web without contacting the web.

Each sensor head 204a-204b further includes a power converter/conditioner 306a-306b. Each power converter/conditioner 306a-306b can be electrically connected to the rails 208a-208b and receive electrical power from the rails. Electrical contacts 312a-312b may be used to contact the rails 208a-208b directly or indirectly, such as via rail contacts 308a-308b. The power converter/conditioner 306a-306b can receive electrical power and convert the electrical power into a form suitable for use in a sensor head 204a-204b. For example, the power converter/conditioner 306a-306b could receive AC power from the power supply 206 and convert the AC power into a DC form. The power converter/conditioner 306a-306b could also receive DC power from the power supply 206 and convert the DC power into a different DC form. However, each sensor head 204a-204b could also or alternatively include an internal power supply or have another source of power and need not receive electrical power over the rails 208a-208b.

The rail contacts 308a-308b respectively couple the sensor heads 204a-204b to the rails 208a-208b so that the sensor heads 204a-204b can move back and forth on the rails. The rail contacts 308a-308b can also optionally be used to provide power from the rails to the electrical contacts 311a-311b. For example, the rail contacts 308a-308b can allow electrical currents to flow between the rails and the power converter/conditioner 306a-306b. Each rail contact 308a-308b includes any suitable structure(s) for coupling a sensor head to a rail. In some embodiments, each rail contact 308a-308b includes a bearing assembly, a bearing wheel, or a slider.

In addition, each sensor head 204a-204b includes a wireless transceiver 312a-312b coupled to one or more antennas 314a-314b. Each wireless transceiver 312 facilitates the wireless transmission and reception of data, such as by transmitting sensor measurements and related data to a control system and receiving commands from the control system (such as one or more controllers 104). Each wireless transceiver 312a-312b includes any suitable structure for generating signals for wireless transmission and for processing signals received wirelessly. In particular embodiments, the wireless transceiver 312a-312b represents a radio frequency (RF) transceiver. Note that the transceiver 312a-312b could be implemented using a transmitter and a separate receiver. Each antenna 314a-314b represents any suitable structure for transmitting and receiving wireless signals, such as an RF antenna.

To support movement of the sensor heads 204a-204b in this example, each sensor head 204a-204b includes a motor controller 316a-316b, which is used to control the operation of a motor 318a-318b. The motor 318a can be used to move the primary sensor head 204a back and forth along the rails 208a-208b, and the motor 318b can be used to move the stand-alone sensor head 204b back and forth along the rails 208a-208b. Each motor controller 316a-316b could generate and output pulse width modulation (PWM) or other control signals for adjusting the direction and speed of the associated motor 318a-318b. The direction and speed could be controlled based on input from a controller as discussed below. Each motor controller 316a-316b includes any suitable structure for controlling the operation of a motor. Note, however, that the sensor heads 204a-204b could be moved in other ways and need not include a motor and motor controller. For instance, one or more external motors could rotate one or more belts coupled to the sensor heads 204a-204b.

Each sensor head 204a-204b includes a controller 310a-310b that controls the overall operation of that sensor head. Each controller 310a-310b could communicate with the controller 104 via the network 106. The controller 310a in the primary sensor head 204a could also be configured to communicate with the controller 310b in one or more stand-alone sensor heads 204b. For example, the controller 310a could receive measurements from one or more sensors 304a and control wireless transmission of the sensor measurements to one or more destinations, such as the controller 104. The controller 310a could also be configured to receive measurements transmitted from a stand-alone sensor head 204b and forward those measurements to one or more destinations, such as the controller 104. In other embodiments, the controller 310b in a stand-alone sensor head 204b could transmit measurements directly to the controller 104.

Each controller 310a-310b could perform a wide variety of other functions. For example, each controller 310a-310b could command the associated motor controller 316a-316b to move a sensor head in a desired direction and at a desired velocity along the rails 208a-208b. As a particular example, the controllers 310a-310b can be pre-programmed to move the sensor heads 204a-204b in particular patterns along the rails 208a-208b. These patterns can be designed to provide an adequate measurement of a particular characteristic of a web 108 while preventing contact or damage to the sensor heads 204a-204b.

Each controller 310a-310b includes any suitable processing or control device(s), such as one or more microprocessors, microcontrollers, digital signal processors, field programmable gate arrays, or application specific integrated circuits. Note that each controller 310a-310b could also be implemented as multiple devices.

In some embodiments, the controller 310a can be configured as a master controller, and the controller 310b can be configured as a slave controller. In these embodiments, the controller 310a could control the speed and direction of the primary sensor head 204a as well as the speed and direction of the stand-alone sensor head(s) 204b along the rails 208a-208b.

In some embodiments, the sensor heads 204a-204b can simultaneously and independently move along the same rails or other support structures across the width (or a portion of the width) of the web 108. This can be done without the sensor heads 204a-204b making contact with or damaging each other. In particular embodiments, both controllers 310a-310b can independently determine the speed and direction of the sensor heads 204a-204b. For example, the controllers 310a-310b could continuously or frequently communicate with each other to determine each other's position along the rails, as well as each other's speed and direction of movement along the rails. This could allow, for instance, a faster moving sensor head 204b to share the rails with a slower sensor head 204a without contact or damage.

In some embodiments, the controllers 310a-310b can be configured to command the respective sensor heads 204a-204b to move at particular speeds and change directions and speeds. The sensor heads 204a-204b can also be directed by the controller 104 via the network 106.

Although FIGS. 3A and 3B illustrate examples of sensor heads of a scanner, various changes may be made to FIGS. 3A and 3B. For example, various components in FIGS. 3A and 3B could be combined, further subdivided, or omitted and additional components could be added according to particular needs. Note that additional details regarding the supply of power to a sensor head over rails can be found in U.S. patent application Ser. No. 13/900,190 (which is hereby incorporated by reference in its entirety). Also, additional details regarding an integrated sensor assembly can be found in U.S. Pat. No. 8,219,025 (which is also hereby incorporated by reference in its entirety).

Figure 4A:
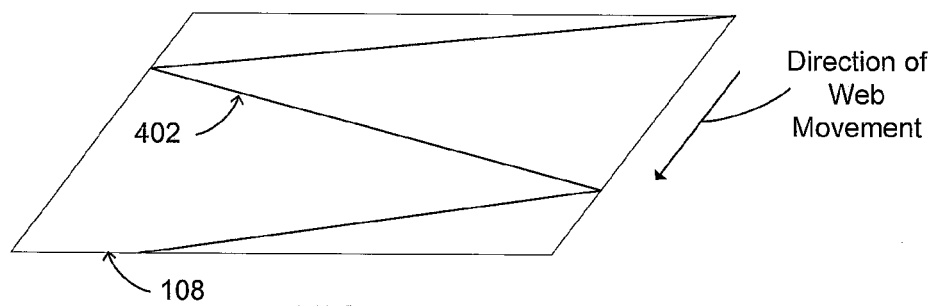
FIGS. 4A through 4C illustrate first examples of traced movements of sensors with respect to a web according to this disclosure.
Figure 4B:
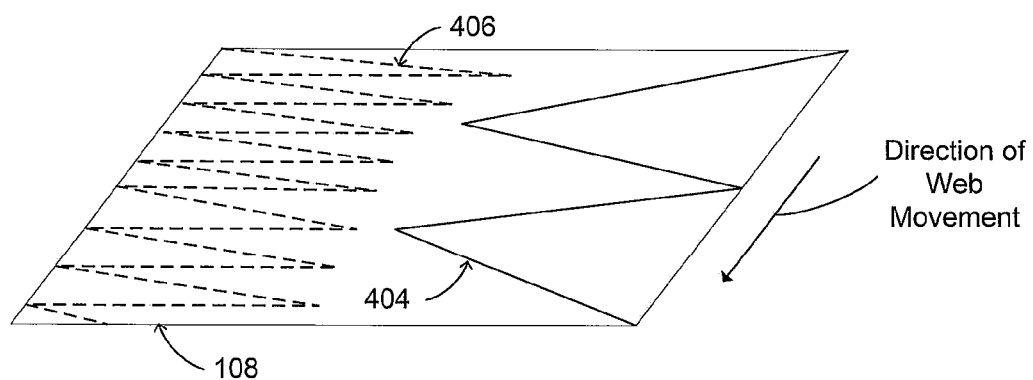
Figure 4C:
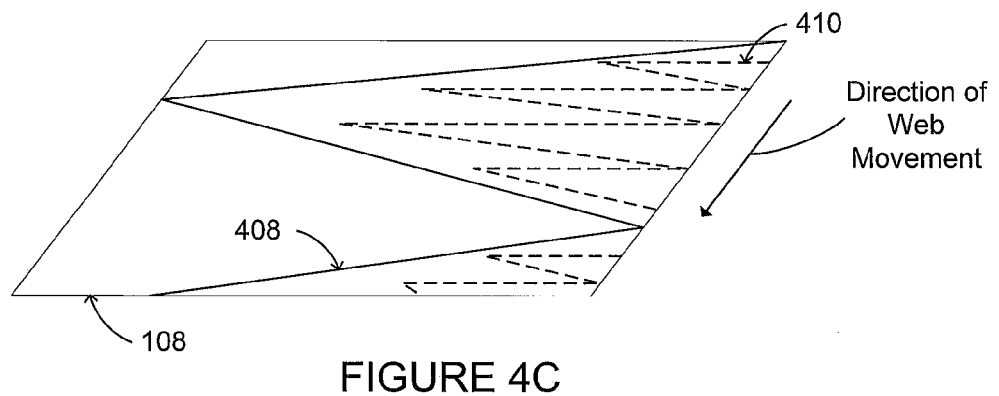

FIGS. 4A through 4C illustrate first examples of traced movements of sensors with respect to a web according to this disclosure. As previously discussed, the sensor heads 204a-204b can move across a web on a common support independently of one other and simultaneously with each other. FIGS. 4A through 4C are non-limiting examples of how the sensor heads 204a-204b could move across a web.

FIG. 4A illustrates an example traced movement 402 of a primary sensor head 204a along a support while a web 108 moves in a machine direction (MD). In this example, a stand-alone sensor head 204b can be positioned at or near an end of the support, for example, allowing the primary sensor head 204a to move across most or all of the width of the web 108. FIG. 4B illustrates an example traced movement 404 of a primary sensor head 204a and an example traced movement 406 of a stand-alone sensor head 204b as the web 108 moves along the machine direction. As shown in this example, the traced movements 404-406 of the sensor heads 204a-204b cover non-overlapping width sections of the web 108. A controller (such as controllers 310a-310b or 104) may direct the sensor heads 204a-204b to remain over these sections of the web 108. FIG. 4C illustrates an example traced movement 408 of a primary sensor head 204a and an example traced movement 410 of a stand-alone sensor head 204b as the web 108 moves in the machine direction. In this example, the sensor heads 204a-204b cover overlapping width sections of the web 108. The sensor heads 204a-204b may or may not include common sensors that measure the same characteristic of the web 108.

The combination of the primary sensor head 204a and the stand-alone sensor head 204b can provide more coverage over the web 108 as the web 108 moves. For example, the stand-alone sensor head 204b may move faster than the primary sensor head 204a. As illustrated in FIG. 4C, for instance, the stand-alone sensor head 204b moves back and forth multiple times while the primary sensor head 204a moves back and forth only once. In an embodiment, the primary sensor head 204a can be a lower resolution sensor head than the stand-alone sensor head 204b such that the stand-alone sensor head 204 is used when a higher resolution sensor for better accuracy or inspection is needed.

Although FIGS. 4A through 4C illustrate first examples of traced movements of sensors with respect to a web, various changes may be made to FIGS. 4A through 4C. For example, these traced movements are for illustration only. Any number of primary sensor heads and stand-alone sensor heads could be used in any other suitable manner.

Figure 5:
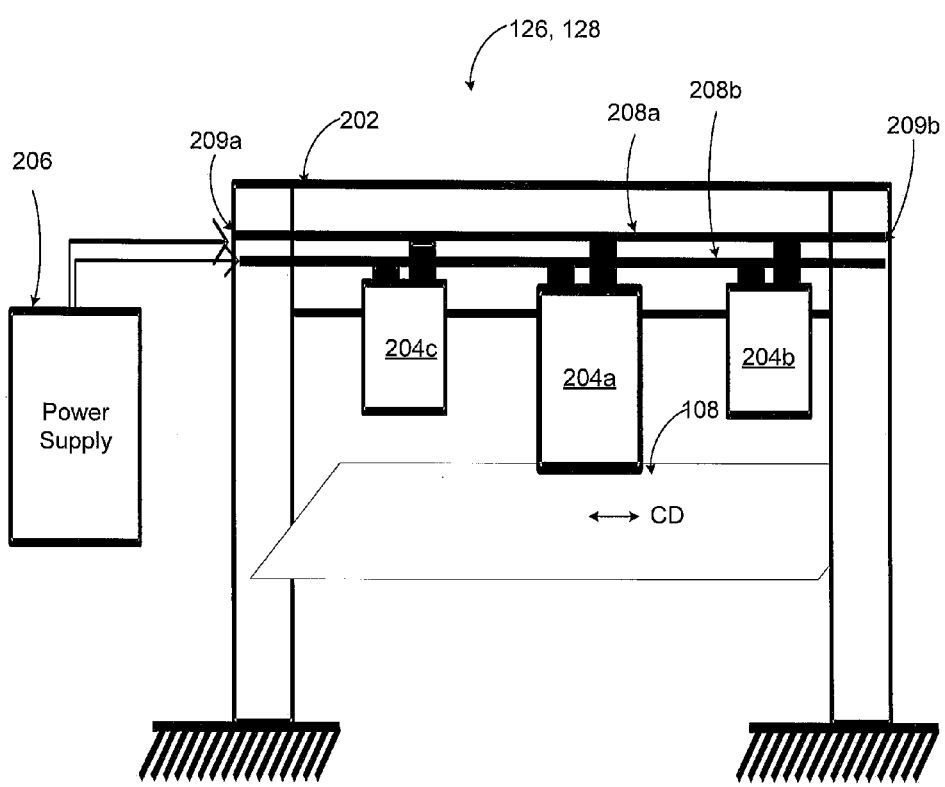
FIG. 5 illustrates a second example arrangement of sensors on a common support of a scanner according to this disclosure.

FIG. 5 illustrates a second example arrangement of sensors on a common support of a scanner according to this disclosure. The example illustrated in FIG. 5 is similar to the example illustrated in FIG. 2. However, FIG. 5 also illustrates an additional stand-alone sensor head 204c added to the rails 208a-208b shared by the primary sensor head 204a and the stand-alone sensor head 204b. While the additional stand-alone sensor head 204c has been added to the rails from the side 209a, an additional stand-alone sensor head can also or alternatively be added to the rails from the side 209b.

Any of the sensors (such as those in the primary sensor head 204a, the stand-alone sensor head 204b, or the stand-alone sensor head 204c) can also be removed from the rail, such as for repair, for replacement, or to add a different sensor. Also, in addition to the sensor heads 204a-204c, still other stand-alone sensor heads can be added to same rails. Any suitable arrangement of primary and stand-alone sensor heads could be used on the same rails or other support.

Once again, the primary sensor head 204a may or may not relay data between the stand-alone sensor heads 204b-204c and an external destination, such as the controller 104. Also, the primary sensor head 204a may or may not communicate with the stand-alone sensor heads 204b-204c, such as to monitor the positions of the stand-alone sensor heads 204b-204c and ensure that contact is minimized between sensor heads. This functionality could be implemented in any of the sensor heads or in any external system, such as the controller 104.

Although FIG. 5 illustrates a second example of an arrangement of sensors on a common support of a scanner 126, 128, various changes may be made to FIG. 5. For example, while the sensor heads 204a-204c are shown as effectively "hanging off" the rails 208a-208b, the rails 208a-208b could be located under the sensor heads 204a-204c, or the sensor heads 204a-204c could have some other arrangement with the rails 208a-208b. Also, the scanner could include any number of primary and stand-alone sensor heads.

Figure 6A:
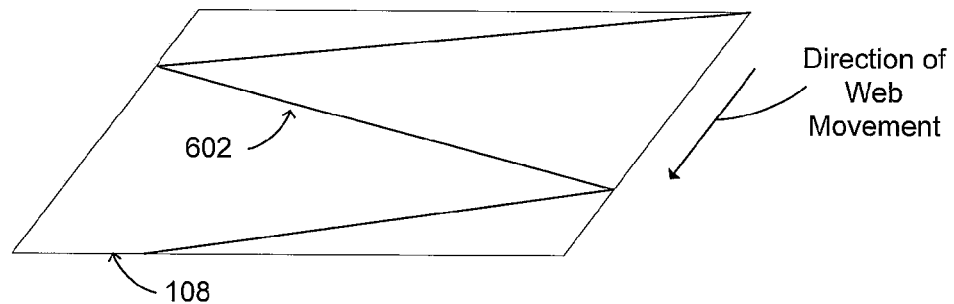
FIGS. 6A through 6C illustrate second examples of traced movements of sensors with respect to a web.
Figure 6B:
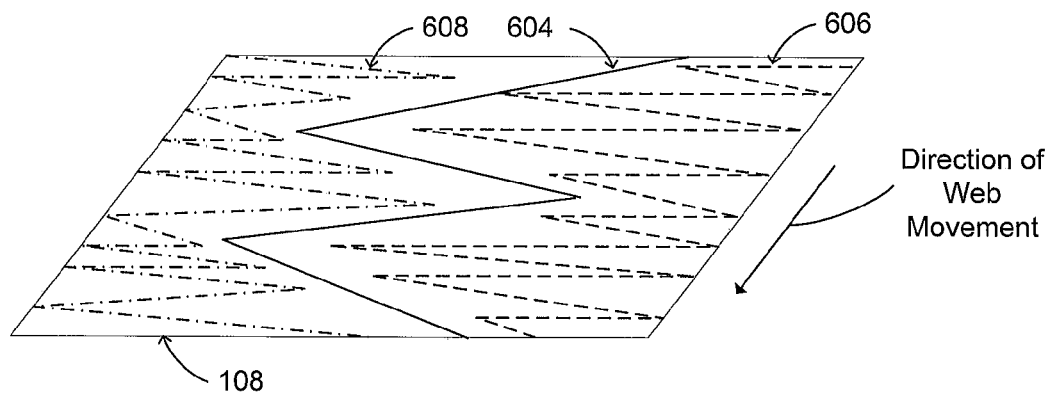
Figure 6C:
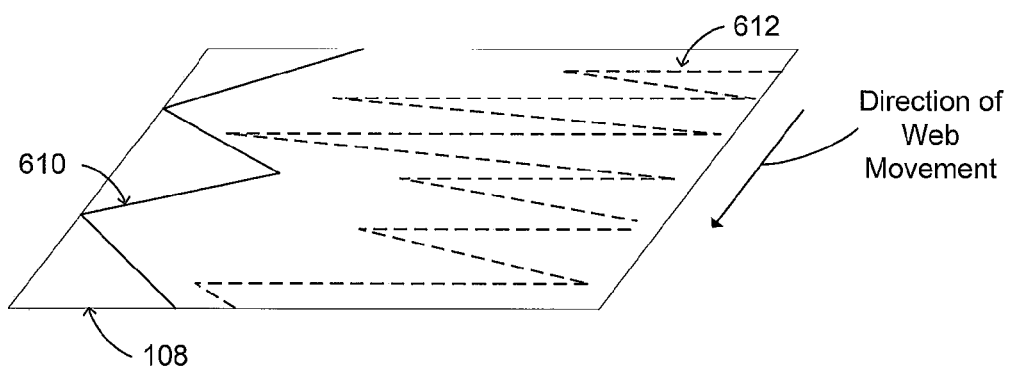

FIGS. 6A through 6C illustrate second examples of traced movements of sensors with respect to a web. All of the sensor heads 204a-204c could be moved independently and simultaneously on their shared support. FIGS. 6A through 6C are non-limiting examples of how the sensor heads 204a-204c could move across a web.

FIG. 6A illustrates an example traced movement 602 of a primary sensor head 204a along a support while the web 108 moves along the machine direction. In this example, the stand-alone sensor heads 204b-204c can be positioned at or near one or more ends of the support, for example, allowing the primary sensor head 204a to move across most or all of the width of the web 108.

FIG. 6B illustrates an example traced movement 604 of the primary sensor head 204a, an example traced movement 606 of the stand-alone sensor head 204b, and an example traced movement 608 of the stand-alone sensor head 204c. FIG. 6C illustrates an example traced movement 610 of the primary sensor head 204a and an example traced movement 612 of the stand-alone sensor head 204b without any movement of the stand-alone sensor head 204c. As can be seen here, multiple sensor heads can be moved in a variety of patterns and at equal or different speeds depending on the implementation.

Although FIGS. 6A through 6C illustrate second examples of traced movements of sensors with respect to a web, various changes may be made to FIGS. 6A through 6C. For example, these traced movements are for illustration only. Any number of primary sensor heads and stand-alone sensor heads could be used in any other suitable manner.

Figure 7:
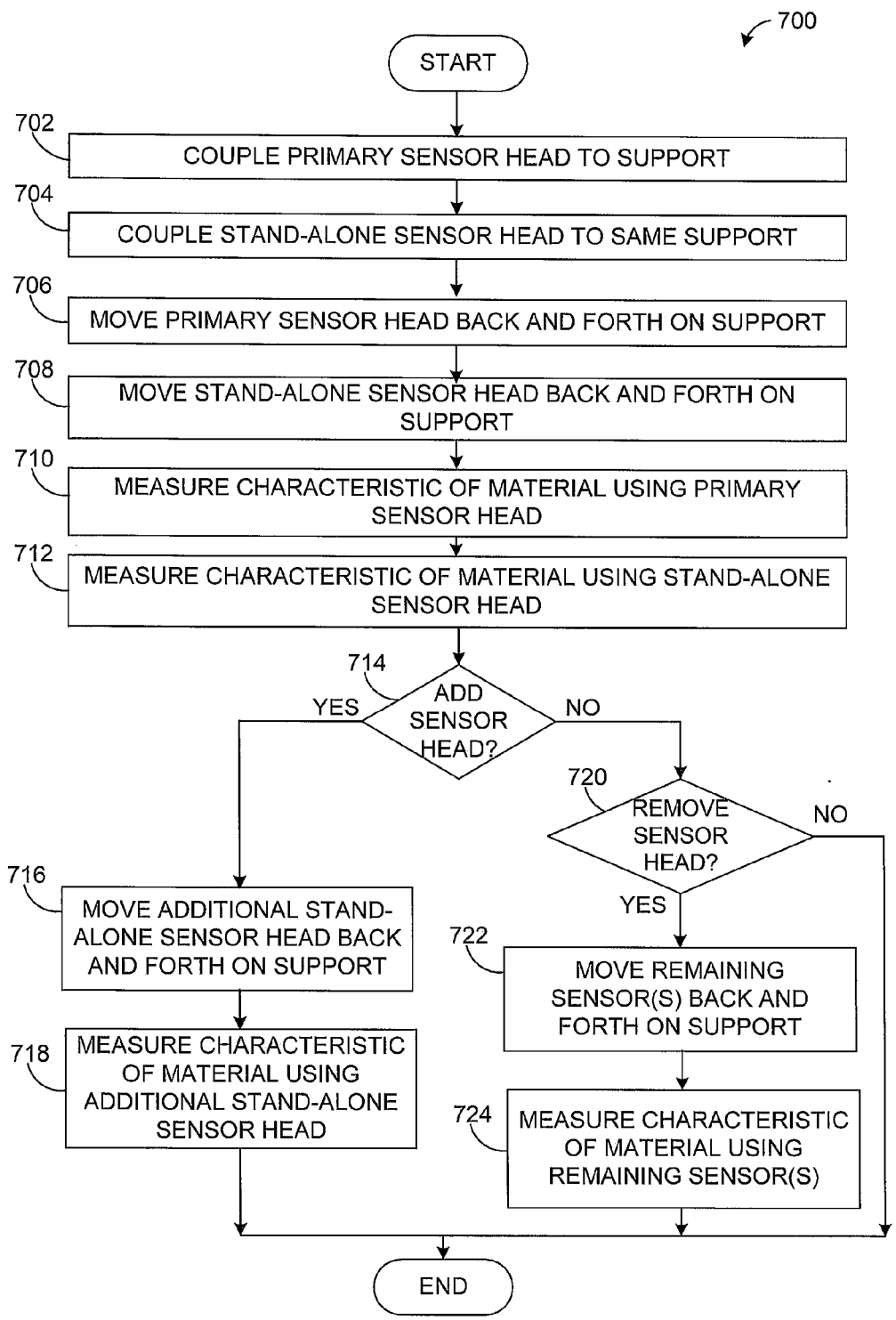
FIG. 7 illustrates an example method for measuring one or more characteristics of a web using multiple sensors on a common support of a scanner according to this disclosure.

FIG. 7 illustrates an example method 700 for measuring one or more characteristics of a web using multiple sensors on a common support of a scanner according to this disclosure. As shown in FIG. 7, at least one primary sensor head is coupled to a support structure at step 702, and at least one stand-alone sensor head is coupled to the support structure at step 704. This could include, for example, personnel mounting at least one primary sensor head 204a and at least one stand-alone sensor head 204b-204c to one or more common rails 208a-208b.

The at least one primary sensor head moves back and forth along the support at step 706, and the at least one stand-alone sensor head moves back and forth along the support at step 708. Each sensor head 204a-204c could move along part or all of the width of the web depending on the configuration, and their paths may or may not overlap. The sensor heads 204a-204c could also move at a common speed or at different speeds.

The at least one primary sensor head measures at least one characteristic of the web at step 710, and the at least one stand-alone sensor head measures at least one characteristic of the web at step 712. For example, each sensor head 204a-204c could include one or more common types of sensors, or different sensor heads 204a-204c could include different types of sensors.

If an additional sensor head is added at step 714, the additional sensor head moves back and forth along the support at step 716, and the additional sensor head measures at least one characteristic of the web at step 718. For example, the additional sensor head could be added prior to maintenance of the primary sensor head 204a or a stand-alone sensor head 204b-204c.

If a sensor head is removed at step 720, one or more remaining sensor heads move back and forth along the support at step 722, and the one or more remaining sensor heads measure at least one characteristic of the web at step 724. For example, the removed sensor head could represent a sensor head that is being placed in an off or idle state, such as when a product specification change is no longer occurring.

Although FIG. 7 illustrates one example of a method 700 for measuring one or more characteristics of a web using multiple sensors on a common support of a scanner, various changes may be made to FIG. 7. For example, while shown as a series of steps, various steps in FIG. 7 could overlap, occur in parallel, occur in a different order, or occur any number of times.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system comprising:
   at least one common support configured to span at least a width of a web of material in a manufacturing or processing system, wherein the at least one common support is stationary; and
   multiple sensor heads each configured to move independently along at least part of the at least one common support;
   wherein a first of the sensor heads is configured to move back and forth once along at least part of the at least one common support during a first time period and a second of the sensor heads is configured to move back and forth multiple times along at least part of the at least one common support during the first time period.

2. The system of claim 1, wherein the sensor heads are configured to move simultaneously along the at least one common support.

3. The system of claim 2, further comprising:
   at least one controller configured to control movement of the sensor heads so that the sensor heads do not contact one another.

4. The system of claim 1, wherein each sensor head comprises one or more sensors configured to measure one or more characteristics of the web.

5. The system of claim 4, wherein different ones of the sensor heads comprise different types of sensors that are configured to measure different characteristics of the web.

6. The system of claim 1, wherein at least one of the sensor heads is configured to move to an end of the at least one common support such that the at least one of the sensor heads is not positioned to measure a characteristic of the web.

7. The system of claim 1, wherein the sensor heads are configured to move in non-overlapping patterns over or under the web.

8. The system of claim 1, wherein the at least one common support comprises one or more rails.

9. The system of claim 1, wherein different ones of the sensor heads are configured to move at different speeds along the at least one common support.

10. The system of claim 1, wherein each sensor head comprises a wireless transceiver configured to wirelessly transmit sensor measurements and head position information.

11. The system of claim 1, wherein ranges of motion of the sensor heads along the at least one common support are collinear.

12. An apparatus comprising:
a first sensor head configured to move along at least one common support spanning at least a width of a web of material in a manufacturing or processing system, wherein the at least one common support is stationary;
wherein the first sensor head comprises:
one or more sensors configured to measure one or more characteristics of the web; and
a controller configured to cause the first sensor head to move along at least part of the at least one common support independently of a second sensor head on the at least one common support;
wherein the first sensor head is configured to move back and forth once along at least part of the at least one common support during a first time period in which the second sensor head moves back and forth multiple times along at least part of the at least one common support.

13. The apparatus of claim 12, wherein the controller is configured to cause the first sensor head to move simultaneously with the second sensor head on the at least one common support.

14. The apparatus of claim 12, wherein the controller is configured to cause the first sensor head to move to an end of the at least one common support such that the first sensor head is not positioned to measure the one or more characteristics of the web.

15. The apparatus of claim 12, wherein the first sensor head is configured to move along one or more rails forming the at least one common support.

16. The apparatus of claim 12, wherein the first sensor head further comprises a wireless transceiver configured to wirelessly transmit sensor measurements.

17. The apparatus of claim 12, wherein the first sensor head further comprises:
a motor configured to move the first sensor head; and
a motor controller configured to control a speed and direction of the motor.

18. The apparatus of claim 12, wherein the first sensor head further comprises a power converter/conditioner configured to receive operating power for the first sensor head from the at least one common support.

19. A method comprising:
independently moving first and second sensor heads back and forth along at least one common support, the at least one common support configured to span at least a width of a web of material in a manufacturing or processing system, wherein the first sensor head moves back and forth once along at least part of the at least one common support during a first time period and the second sensor head moves back and forth multiple times along at least part of the at least one common support during the first time period, wherein the at least one common support is stationary; and
measuring one or more characteristics of the web of material using the first and second sensor heads.

20. The method of claim 19, wherein:
independently moving the first and second sensor heads back and forth comprises simultaneously moving the first and second sensor heads back and forth along the at least one common support; and
the first and second sensor heads are controlled so that the sensor heads do not contact one another.

21. The method of claim 19, wherein independently moving the first and second sensor heads back and forth comprises moving the first and second sensor heads back and forth in non-overlapping patterns over or under the web.

* * * * *